United States Patent [19]

O'Connor et al.

[11] Patent Number: 5,627,026

[45] Date of Patent: May 6, 1997

[54] DETECTION OF BOTH AN ANTIBODY AND AN ANTIGEN IN A SINGLE SAMPLE ALIQUOT

[75] Inventors: Thomas P. O'Connor, Yarmouth; Quentin J. Tonelli, Portland, both of Me.

[73] Assignee: IDEXX Laboratories, Inc., Westbrook, Me.

[21] Appl. No.: 364,432

[22] Filed: Dec. 27, 1994

Related U.S. Application Data

[63] Continuation of Ser. No. 83,790, Jun. 28, 1993, abandoned, which is a continuation of Ser. No. 219,100, Jul. 14, 1988, abandoned.

[51] Int. Cl.$^6$ .......................... C12Q 1/70; G01N 33/569
[52] U.S. Cl. ......................... 435/5; 435/7.94; 436/518; 436/820
[58] Field of Search ................... 435/5, 7.4, 7.1, 435/235.1, 805; 436/518, 548, 544, 820, 501, 536, 540, 545, 810, 811; 530/387.1, 388.3, 388.35

[56] References Cited

U.S. PATENT DOCUMENTS

| Re. 32,696 | 6/1988  | Schuurs et al.    | 435/7   |
|------------|---------|-------------------|---------|
| 4,299,916  | 11/1981 | Litman et al.     | 435/6   |
| 4,376,110  | 3/1983  | David et al.      | 436/513 |
| 4,769,216  | 9/1988  | Chandler et al.   | 422/58  |
| 4,879,212  | 11/1989 | Wang et al.       | 435/5   |
| 4,904,581  | 2/1990  | Burger et al.     | 435/5   |
| 4,917,998  | 4/1990  | Burger et al.     | 435/5   |
| 4,923,798  | 5/1990  | Le Moine et al.   | 435/5   |
| 5,486,452  | 1/1996  | Gordon et al.     | 435/5   |

FOREIGN PATENT DOCUMENTS

| 0171150 | 2/1986  | European Pat. Off. . |
| 0173295 | 3/1986  | European Pat. Off. . |
| 0200381 | 11/1986 | European Pat. Off. . |
| 0286264 | 10/1988 | European Pat. Off. . |
| 2051357 | 1/1981  | United Kingdom .     |

OTHER PUBLICATIONS

Odell et al., eds., Principles of Competitive Protein Binding Assays, John Wiley and Sons, New York, 1983, pp. 243–254.
Lerner, Nature 299:592, 1982.
Shaw et al., Science 226:1165, 1984.
Pederson et al., 235 Science 790, 1987.
Pederson et al., U.S. Patent Application Ser. No. filed Aug. 26, 1987, entitled "Feline T–Lymphotropic Lentivirus".
Wilson et al., "Recent Developments in the Periodate Method of Conjugating Horseradish Peroxidase", North Holland Biomedical Press, pp. 215–223 (1978).
Hardy "Feline T–Lymphotropic Lentivirus": Retrovirus–Induced Immunosuppression in Cats, Journal of the American Animal Hospital Association, pp. 241–243, vol. 24, (1988).
UC Clip Sheet (Trends) 1987.
Harbour et al., "Isolation of a T–lymphotropic lentivirus from a persistently leucopenic domestic cat", Veterinary Record, 122:84–86 (1988).
The Veterinary Record, "Implications of the isolation of FTLV", vol. 122, No. 4, (1988).
Sparger, "Feline T–lymphotrophic Lentivirus Infection", Feline Medicine IV; Veterinary Learning System, 1988, pp. 9–14.
Yamamoto et al., Am. J. Vet. Res. vol. 49, No. 8, Aug. 1988, pp 1246–1258.

*Primary Examiner*—Marian C. Knode
*Assistant Examiner*—Donna C. Wortman
*Attorney, Agent, or Firm*—Fish & Richardson P.C.

[57] ABSTRACT

A method for detecting the presence of antibody to FIV in a biological sample. The method includes the steps of providing a first antigen having a first epitope recognized by the antibody, the first antigen being detectable; contacting the first antigen with the sample under conditions under which the antibody can bind to the first antigen to form an immune complex; and detecting the immune complex. An ELISA test for FIV, using purified FIV antigen, is also described.

15 Claims, 1 Drawing Sheet

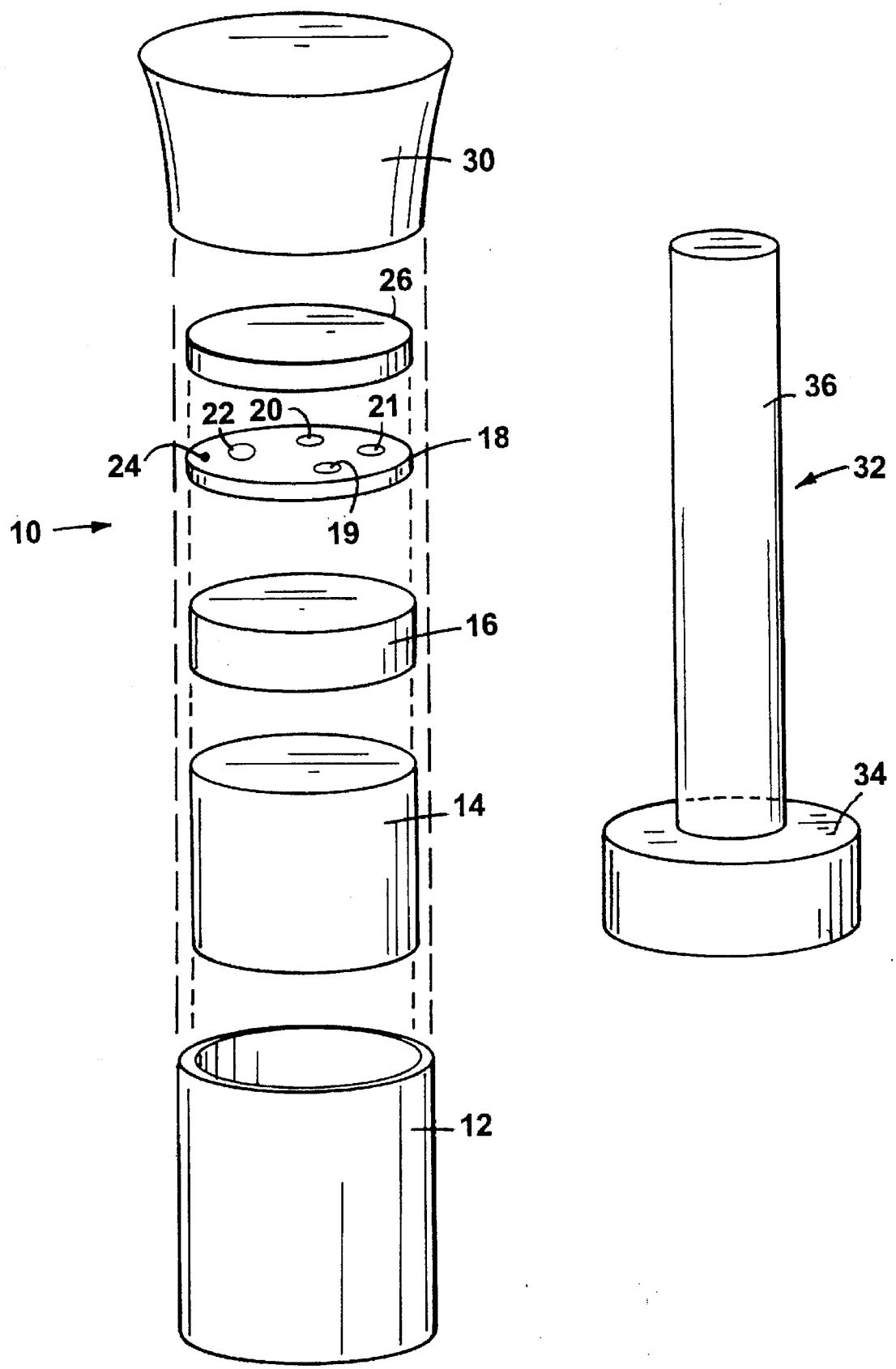

DETECTION OF BOTH AN ANTIBODY AND AN ANTIGEN IN A SINGLE SAMPLE ALIQUOT

This is a continuation of application Ser. No. 08/083,790, filed Jun. 28, 1993, now abandoned which is a continuation of application Ser. No. 07/219,100, filed Jul. 14, 1988, now abandoned.

BACKGROUND OF THE INVENTION

This invention concerns immunoassay methods for the detection or measurement of substances in liquid samples, e.g., biological fluids such as whole blood, serum, plasma, and urine.

A wide variety of substances are commonly detected or measured by immunoassay methods, for example, hormones, antibodies, toxins, drugs, and antigens such as viral particles. Usually, although not always, either the substance being detected or a substance used in its detection is an antibody, hence the term "immunoassay." The antibody is a member of a specific binding pair, the other member of the pair being referred to as an antigen, or analyte. Other specific binding pairs, besides antibodies-antigen pairs, which are measured and used in similar assays, include pairs of molecules which have specific binding affinity for each other, e.g., hormones and hormone receptors, and biotin and avidin.

Immunoassays are commonly carried out, at least in part, on solid supports, e.g., glass fiber membranes. The two most common formats for immunoassays employing solid supports are competitive and sandwich formats. Typical competitive formats are described e.g., in Littman et al., U.S. Pat. No. 4,540,659, and a typical sandwich assay by David et al., U.S. Pat. No. 4,376,110.

Examples of the use of a sandwich test are an immunofluorescent assay (IFA) and an enzyme-linked immunosorbent assay (ELISA). Both these assays are used for detection of a common disease of cats, feline leukemia virus (FeLV).

FeLVs are an endogenously replicating C-type oncornavirus; the viral genome is incorporated into the host chromosome as a provirus, and the genome is translated to produce intact virions. The virus is spread horizontally from infected to susceptible cats and causes a number of disease syndromes ranging from myeloid and lymphoreticular neoplasms to an acquired immunodeficiency syndrome.

Another virus which infects cats is a retrovirus recently isolated from a group of cats suffering from immunodeficiency-like syndrome; the virus is termed feline-T-lymphotrophic lentivirus (FTLV or FIV). It belongs to the same group as the human immunodeficiency virus (HIV), the causitive agent of human AIDS. FIV is described by Pederson et al., 235 Science 790, 1987. Antibody to FIV has been detected by use of an IFA.

SUMMARY OF THE INVENTION

In a first aspect, the invention features a method for detecting the presence of antibody to FIV in a biological sample. The method includes the steps of providing a first antigen having a first epitope recognized by the antibody, the first antigen being detectable; contacting the first antigen with the sample under conditions under which the antibody can bind to the first antigen to form an immune complex; and detecting the immune complex.

By "detectable" is meant that the first antigen either is labelled with a label which can be readily detected, for example, a radioisotope, an enzyme, or a fluorophore; or that the antigen can be readily bound to a molecule having such a label, e.g., a labelled antibody to the antigen.

In preferred embodiments, the method further includes, prior to the contacting step, the step of binding the antibody to a solid support. Most preferably, the binding step includes binding a second antigen to the solid support, the second antigen having a second epitope recognized by the antibody, wherein the second antigen can be the same as the first antigen and the second epitope can be the same as the first epitope; and contacting the sample with the second antigen under conditions under which the antibody can bind to the second antigen.

Preferably, the first and second antigens are derived from FIV, or comprise FIV, or a polypeptide substantially the same as a polypeptide derived from FIV. By substantially the same is meant that the polypeptide has an amino acid sequence identical to, or with less than 10% substitutions, compared to the naturally occuring sequence.

In a second aspect, the invention features an antigen which includes an epitope of FIV (the antigen can be FIV itself), the antigen having a detectable label. The antigen can be, in addition to FIV, any polypeptide substantially the same as a polypeptide isolated from FIV, or derived from FIV.

In a third aspect, the invention features a method for simultaneously detecting the presence of a first antibody and a first antigen in a biological sample, the method including the steps of providing a second antigen having a first epitope recognized by the first antibody, the second antigen being detectable; providing a second antibody which specifically recognizes the first antigen, the second antibody being detectable; contacting the second antigen and the second antibody with the sample under conditions under which the second antigen can bind to the first antibody to form a first immune complex and the second antibody can bind to the first antigen to form a second immune complex; and detecting the first or second immune complex.

In preferred embodiments, the method further includes, prior to the contacting step, binding the first antigen and the first antibody to a solid support. Most preferably, the binding step includes binding a third antigen to the solid support, the third antigen having a second epitope recognized by the first antibody, wherein the third antigen can be the same as the second antigen, and the second epitope can be the same as the first epitope; binding a third antibody to the solid support, the third antibody specifically recognizing the first antigen; and contacting the sample with the third antigen and the third antibody under conditions in which the first antibody can bind to the third antigen to form a third immune complex and the first antigen can bind to the third antibody to form a fourth immune complex. Preferably, the third antigen and the third antibody are bound to the solid support at separated positions, wherein binding with the first antibody or the first antigen to the solid support can be distinguished; the first antigen is FeLV and the first antibody is anti-FIV; the first antigen is HIV or Hepatitis antigen, and the first antibody is anti-HIV, or anti-Hepatitis.

In a fourth aspect, the invention features a solid support having a first antigen and a first antibody wherein the first antigen and antibody are available for reaction with a corresponding second antibody to the first antigen and a corresponding second antigen for the first antibody.

In preferred embodiments, the solid support is chosen from a microtiter well, a glass or plastic bead, a filter matrix, a polystyrene latex bead, and other microparticles; the first antigen and the first antibody are bound to the filter matrix at separated positions; the first antigen is FIV, a polypeptide having an epitope of FIV, or is derived from FIV, and the first antibody is anti-FeLV; the first antigen is HIV or HTLV I, a polypeptide having an epitope of HIV or HTLV I, or is derived from HIV or HTLV I, and the first antibody is anti-Hepatitis antigen, anti-HIV, or anti-HTLV-I.

The invention also features a kit including a solid support having a first antigen and a first antibody, wherein the first antigen and antibody are available for reaction with a corresponding second antibody to the first antigen and a corresponding second antigen for the first antibody; and a third antigen having an epitope recognized by the second antibody, the third antigen being detectable, or a third antibody able to specifically react with the second antigen, the third antibody being detectable.

In preferred embodiments, the kit has both a third antigen and a third antibody; the solid support is chosen from a microtiter well, a glass or plastic bead, a filter matrix, a polystyrene latex bead, and other microparticles; the first antigen and the first antibody are bound to the filter matrix at separated positions; the first antigen is FIV, a polypeptide having an epitope of FIV, or is derived from FIV, and the first antibody is anti-FeLV; the first antigen is HIV, a polypeptide having an epitope of HIV, or is derived from HIV, and the first antibody is anti-Hepatitis antigen or anti-HIV; and the solid support has a region including a positive or a negative control spot (as is explained below).

In another aspect, the invention features a method for detecting the presence of antibody to FIV in a biological sample, the method including the steps of providing purified FIV, or a purified antigen from FIV, or a purified polypeptide substantially the same as a polypeptide isolated from FIV, wherein the purified FIV is substantially free from FIV host cell proteins and is composed of at least 5% p26 (the major nucleocapsid protien, as measured by densitometric scans of coomassie blue G-250 stained SDS-PAGE) as total protein; binding the purified FIV, or the antigen or the polypeptide to a solid support; contacting the sample with the solid support under conditions under which the antibody can bind the purified FIV or the antigen or the polypeptide, to form a first immune complex; contacting the first immune complex with an enzyme-labelled antibody under conditions under which the detectable antibody forms a second immune complex with the first antibody; and detecting the second immune complex.

In preferred embodiments, the detectable antibody includes an enzyme, e.g., horseradish peroxidase or alkaline phosphatase; and the detectable antibody is anti-feline antibody.

In yet another aspect, the invention features purified FIV substantially free from FIV-host cell proteins, composed of at least 5% p26 as total protein.

The invention provides a test for detection of FIV in biological samples which has greater specificity and sensitivity than prior tests. By using a labelled antigen able to react with anti-FIV it is possible to form a large immune complex having many labelled molecules; this increases the test sensitivity. The ELISA FIV test of the invention, which uses a greatly purified FIV antigen, and increases sensitivity and specificity over existing methods of testing for FIV.

The present invention also provides a method by which any pair of antigen and antibody may be simultaneously detected in a single blood sample by use of a single testing device. This has not previously been possible, using conventional techniques, since for example, an antigen in whole blood requires use of undiluted blood, whilst assay for an antibody requires use of diluted blood. This invention overcomes this problem by using a labeled antigen, rather than a labelled antibody, to detect antibody in the sample. Thus, for example, whole blood of humans may be simultaneously screened for Hepatitis B antigen and HIV antibody and any blood which is positive for either of these disease-causing agents discarded from, for example, a blood bank. This method can be used to rapidly screen large numbers of biological samples for any desired mixture of antigens and antibodies without loss of sensitivity compared to alternative procedures. A single test thus takes the place of a plurality of prior tests.

The simultaneous assay of the invention provides a means for rapidly screening blood or other biological fluids for infective agents, such as FeLV, FIV, Hepatitis antigen, and HIV. Simultaneous screening for mixtures of antigens and antibodies allows a single test to be performed to determine whether or not the biological sample is useful, e.g., whether human blood can be used in a transfusion. The assay also allows determination of the cause of infection by one or more viruses producing similar clinical symptoms, such as FeLV and FIV. It is also possible to perform a simultaneous assay for antigens and antibodies associated with the same viral infection, e.g., HIV antigen and anti-HIV antibody. (For this assay it is necessary to provide a monoclonal antibody which recognizes the epitope on the HIV antigen which is chemically bound to the enzyme label, for example, a monoclonal antibody directed against p24 (commercially available) can be used.)

The simultaneous FeLV and FIV test of the invention is useful in determining whether a cat with "Sick Cat Syndrome" is infected with a chronic disease (FIV or FeLV) and thus should be isolated from other cats or perhaps destroyed; or is not so infected and can thus be treated with antibiotics. About 12–15% of such cats are infected with FIV, 12–15% with FeLV, and the remainder are not infected with these viruses. Similarly, the test can be used to test a kitten to determine whether to administer an FeLV vaccine to it, and whether to allow the kitten to come in contact with other cats.

Other features and advantages of the invention will be apparent from the following description of the preferred embodiments thereof, and from the claims.

DESCRIPTION OF THE PREFERRED EMBODIMENTS

The drawing is first briefly described.

BRIEF DESCRIPTION OF THE DRAWING

The FIGURE is an exploded isometric view of an assay device suitable for use in the invention.

Simultaneous Assay for FeLV Antigen and FIV Antibody

The following is an example of simultaneous detection of an antigen and an antibody in a single test. In this example, FeLV antigen and antibody to FIV in feline serum, plasma, or whole blood are measured simultaneously in a single test. In this example, the assay uses a solid phase format for immunoassay of FeLV antigen and FIV antibody; other formats are also suitable, for example, a dipstick format as described in U.S. Pat. No. 5,256,372, hereby incorporated by reference; a microtiter well-based format; and the format described in U.S. Pat. Nos. 4,939,096 and 4,965,187, all of which are hereby incorporated by reference.

Referring now to the FIGURE, the FIV/FeLV assay is performed using anti-FeLV monoclonal antibody coated latex particles spotted onto glass fiber filter 18 at position 19. Similarly, on the same filter 18, latex particles coated with FIV antigen are spotted for use in the FIV antibody assay at position 20. The incorporation of both positive and negative control reagents at positions 22 and 21, respectively, on filter membrane 18 allows two complete test procedures to be carried out simultaneously, yielding an unambiguous result.

Still referring to the FIGURE, glass fiber filter 18 is also provided with an orientation spot 24, and is incorporated into cylindrical disposable assay device 10 supported on porous polyethylene disc 16 and cellulose acetate absorbant 14. The combined wicking properties of these materials serve to control the flow of sample and reagents through the membrane. This system minimizes the kinetic problems associated with solid phase immunoassays in that it eliminates the "unstirred" layer of solution at the surface of the solid phase, in which diffusion limits transport of reagents to reactive particle-bound components. The design of the particulate solid phase and its function within the assay device enhance the binding of reagents compared to other solid phases. This configuration may be used for serum, plasma, or whole blood.

In addition to filter 18, cylinder 12 includes accessory prefilter 26, which serves to remove insoluble material from the sample during application. Device 10 is assembled by placing the component parts described above into cylinder 12 fixed to an upper conical-shaped cup 30. A plunger 32 having a handle 36 and a sponge portion 34 is used to seat each of the component parts.

Generally, the conjugate mixture used to detect any bound antigen or antibody on filter 18 contains horseradish peroxidase (HRPO) conjugated monoclonal antibody to p27 (a major core protein of FeLV) and HRPO conjugated FIV antigen. The conjugate and test sample are mixed, and conjugated monoclonal antibody will bind p27 antigen (if present), while conjugated FIV antigen will bind anti-FIV antibody (if present). Upon application of this mixture to assay device 10, the membrane-bound anti-p27 antibody will capture the p27 conjugated antibody complex, and the membrane-bound FIV antigen will capture the anti-FIV conjugated antigen complex. Following a wash step and addition of substrate and chromogen, color development in the FeLV sample spot indicates the presence of FeLV antigen, and color development in the FIV sample spot indicates the presence of FIV antibody.

A feature of this assay is the incorporation of positive and negative controls. Positive control particles are coated with antibody to HRPO. A small amount of conjugate applied to the membrane during the course of the assay is captured by the positive control spot. Subsequent color development by the positive control indicates that the conjugate is active; this is one criterion for assay validity. The negative control particles are coated with non-specific mouse antibody and purified uninfected host cell antigen. The amount of mouse antibody and host cell antigen coated on these particles is sufficient to mimic "nonspecific" reactions that may occur with either sample particle. The negative control spot is exposed to all assay reagents in a fashion identical to the sample spots. The negative control spot should remain clear, or less colored than the sample spots for a positive result to be valid. Substantial coloration in the negative control spot indicates a nonspecificity problem and may invalidate the test. User interpretation of assay results is as follows: (1) positive control only develops color, negative result; (2) positive control and FeLV and/or FIV sample spot(s) develop color, positive result for respective sample spot; (3) negative control develops color more intense than sample spot, negative result; (4) no color development in any spot, invalid test; (5) negative control develops color less intense than sample spot(s), positive result for respective sample spot.

The individual components of the assay will now be discussed, and a detailed example of the assay provided.

FIV Virus Antigen

The FIV antigen employed is FIV virus (particles), or is derived from FIV virus particles, as follows. (Synthetic antigens are also suitable in the assay, as are substantially purified polypeptides derived from FIV particles.) Master seed virus producing cultures were obtained in the form of a continuous feline cell line infected with FIV Isolate No. 2427 (petaluma strain) from Dr. Niels Pederson (University of California, Davis, Calif.). Other virus cultures can be obtained as described by Pederson, supra, or by Harbour et al., 122, The Veterinary Record 84, 1988. Seed stocks of virus producing cell cultures were obtained by freeze-downs of FIV-infected master seed cell cultures following at least 19 post infection passages in culture. Additional seed stocks of virus producing cultures are obtained by either infection of the continuous feline cell line with FIV master seed virus or by single cell microwell cloning of high level FIV producers from the original FIV infected master seed cell culture. For propagation, master seed virus infected feline cell cultures are inoculated into tissue cell culture flasks. Following growth to a confluent monolayer of cells, tissue culture fluid is harvested at intervals of 2–5 days.

Working seed virus is produced by propagation by the master seed cell line permanently infected with FIV. An inoculum is added to tissue culture flasks, incubated, and the spent tissue culture fluid harvested. Typically the flasks are incubated at 36° C.–38° C. for a maximum of 7 days before fluid and cell harvest. The harvested fluid, including cell material, is centrifuged in a high speed centrifuge (Sorval RC-5B or Beckman J2-21) leading to separation of supernatant and cell pellet material. The cell pellet is discarded, and the supernatant culture fluid used to prepare working virus. The clarified supernatant is made 0.5 M in NaCl and 4%–10% in polyethylene glycol (PEG 8000, Sigma). Following overnight precipitation, virus is pelleted and resuspended in buffer 10 mM TrisCl, 300 mM NaCl, 1mM EDTA, pH 7.5. The virus is then centrifuged (at 13,000×g for 15 min.) After centrifugation the pellet is discarded and the clarified supernatant centrifuged in a 50%–90% discontinuous gradient of glycerol. Centrifugation is at 75,000×g for 3 hrs. and the FIV viral band at the interface collected. The band is suspended in buffer and centrifuged at 75,000×g for 1 hr; the resulting pellet is resuspended in buffer and stored at −70° C.

Polystyrene Particles

Polystyrene particles (0.2–2 microns from Pandex Laboratories) are suspended in 10 mM potassium phosphate buffer, pH 7.2, and mixed with 50–1000 μg of inactivated FIV particles. FIV is inactivated by provision of 0.25% sodium dodecyl sulfate (SDS) and heating at 56° C. for 1 hr. The amount of SDS may be varied proportional to the protein content of the FIV particles. Generally, 2.4 mg of SDS are used per mg of antigen. After incubation at 15° C.–30° C. for 1–24 hrs. the particles are centrifuged at 13,000×g for 10 min. The pellet is resuspended in 1% Bovine serum albumin (BSA), 10 mM potassium phosphate buffer, pH 7.2, incubated at 15° C.–30° C. for 0.5–2 hrs., and centrifuged as above. The pellet is washed in buffer and centrifuged again. The resulting pellet is then resuspended in 2.5% sucrose 10 mM potassium phosphate buffer and 0.05% Tween 20. 2.5–6 µl of a 1% solution of the resulting particles are spotted onto the assay device.

FIV Antigen Conjugate

Purified FIV virus is inactivated by addition of detergent and heat treatment at 65° C. for 90 min. Virions are further disrupted by the addition of surfactant. For example, 2 ml of FIV antigen is added to 4.8 mg SDS, heated at 65° for 90 min., and allowed to cool for 2 hrs. at 4° C. After centrifugation of 4° C. for 10 min. in a microcentrifuge tube, Triton® X-100 (polyoxethylene ethers) is added to a final concentration of 1.5% and the mixture allowed to stand at 15° C.–30° C. for 30 min. 0.9 mg of Bio-beads (Bio-Rad S-100, Bio-Rad Laboratories) are added per ml of solution, and the mixture shaken for 2 hrs. The solution is removed and dialyzed overnight against 25 mM $NaHCO_3$, pH9.2. The clarified antigen is then treated with metaperiodate activated horse radish peroxidase by the method of Wilson et al. (Immunofluorescence and Related Staining Techniques, ed. Knapp et al., p. 215, 1978), and the conjugate treated with sodium borohydride and diluted in conjugate diluent (10 mM TrisCl, pH 7.2–7.6 containing 0.05% Tween® 20 (polyoxyethylenesorbitan), 50% calf serum, 10% mouse serum, 0.1 mg D & L Blue dye, 16 mg/l gentamicin (Sigma) and 0.2 g/l Thimerosol (Sigma)).

FeLV Antibody

Monoclonal antibody producing cell lines against FeLV virus p27 antigen were obtained from the School of Veterinary Medicine, University of California, Davis, California. These cell lines are available from the University of California. The cell lines are initially propogated in tissue culture and then injected into pristane primed BALB/C or IRC/Fl mice. The asches fluid is harvested and clarified. The antibody is partially purified by either ammonium sultate precipitation or column chromatography using affinity or ion exchange gels. Particles are prepared as described above for FIV. The coating buffer contains the mouse antibody to FeLV. Other suitable monoclonal antibodies to FeLV can be prepared by standard techniques from FeLV viral particles (available from Electro Nucleonics Inc., Silver Spring, Md.).

FeLV Conjugate

Monoclonal anti-FeLV horse radish peroxidase conjugate is prepared as described above for FIV conjugate.

Control Particles

Negative particles as a control for the FIV test are coated with an extract of an uninfected cell line. Negative particles for the FeLV test are coated with IgG non-reactive to FeLV (purchased from Sigma).

Positive particles for the FIV and FeLV tests are coated with anti-horse radish peroxidase as described above. Positive particles are manufactured with anti-horse radish peroxidase purchased from Atlantic Antibodies or from Jackson Laboratories (Pennsylvania).

Preparation of Assay Device

The assay device described above is spotted with dyed reference particles to form an orientation spot. Positive particles, FIV particles, FeLV particles, and negative particles are then also applied. The negative particles are prepared by mixing equal volumes of FeLV negative particles and FIV negative particles.

Assay Protocol

The device is wetted with 0.5 ml of wash solution [2 M potassium chloride, 2.5% non-fat dry milk, 5% BSA, 0.5% Triton® X-100 (polyoxethylene ethers), 0.1 Tween® 80, (polyoxyethylenesorbitan), 0.5% Kathon, and 0.16 g/l gentamicin] and the prefilter seated in the device. 0.15 ml of conjugate is then placed into a sample tube and 0.2 ml of the sample to be assayed added. The tube is capped and the contents mixed thoroughly by inverting 4–5 times. The tube is then incubated for 3–5 min. at 15° C.–30° C. and the entire contents of the tube added to the assay device, and allowed to incubate for 3–5 min. at 15° C.–30° C. The prefilter is then removed and 0.5 ml of wash solution added and allowed to be absorbed. The assay device is then filled with 2 ml of wash solution. After the wash solution has been absorbed 0.15 ml of TMB substrate (1 g/l tetramethylbenzadine (TMB) in 60% methanol and 40% glycerol) diluted 1:1 in TMB diluent (0.1M dibasic potassium phosphate, 0.1M citric acid, 30% hydrogen peroxide and 0.1 g/l thimerosal) is added. The device is incubated for 3 min. at 15° C.–30° C. and the reaction stopped by addition of 0.5 ml of stop solution (0.05–0.1M ammonium molybdic acid). The result is then read.

ELISA Test for FIV

The following is an example of an ELISA test for FIV antibody in whole blood of a cat. In this test, it is important that the viral antigen be purified sufficiently to be free from host cell proteins in order to reduce background reactions. Generally, purity of the purified virus is confirmed by polyacrylamide gel electrophoresis of the major proteins. The preparation is sufficiently pure when the nucleocapsid or gag gene products, most preferably the p26 nucleocapsid protein, represents at least 5%, preferably 12%–15%, of total protein in the vital preparation. One method for purification of the virus is by density gradient centrifugation in a relatively high ionic strength buffer container glycerol, for example, by collecting the virus at a 50%–90% glycerol interface in 10 mM TrisCl, 300mM NaCl and 1mM EDTA buffer, pH 7.5, as described above.

In one format of an ELISA test (the test unit is available from Agritech Systems, Portland, Me.), FIV antigen is coated, by standard procedures, onto wells in a microtiter dish and incubated with the sample to be tested. Any antibody in the sample specific to FIV forms complexes with the coated vital antigens. Following a wash procedure, an anti-feline horseradish peroxidase conjugate is added to the wells such that it binds to feline antibody bound to the FIV antigen coated in the well. In the final step of the assay, unbound anti-feline conjugate is washed away and enzyme substrate (hydrogen peroxide) and a chromogen (tetramethylbenzadine, TMB) are added. Subsequent color development is proportional to the amount of specific antibody present in the sample.

The controls include an antigen-coated well treated with 100 µl of a negative control composed of non-FIV reactive feline serum in phosphate buffered saline (PBS, 0.01M sodium phosphate, 0.15M NaCl, pH 7.2–7.6) containing 5% fetal calf serum (FCS); and at least one antigen coated well treated with 100 µl of a positive control composed of feline anti-FIV antibody positive serum in PBS and FCS.

In the assay, 100 µl of diluted serum or plasma sample is dispensed into each well. The diluent is PBS and FCS, and generally the sample is diluted 100-fold. The wells are incubated for 30 min. at 15° C.–30° C., and the liquid contents of all the wells is then aspirated into a waste reservoir and each well is washed five times with approximately 300 μl of diluted wash solution (PBS+0.05% Tween® 20(polyoxyethylenesorbitan)). The liquid is aspirated from the wells following each wash. Following the final wash, residual wash fluid is removed from the well onto absorbent paper, and 100 μl of anti-feline HRPO conjugate is added to each well (0.1–2.0 μg/ml) and incubated for 30 min. at 15° C.–30° C. The wells are then aspirated and washed again. 50 μl of TMB diluent solution is then added to each well, followed by 50 μl of TMB substrate. After incubation for 15 min. at 15°–30° C., 100 μl of stop solution (1 in 400 aqueous dilution of hydrofluoric acid) is added to each well. The absorbance value at 650 nm ($A_{650}$) is read for the samples and controls. For the assay to be valid, the difference between the positive control and the negative control should be greater than 0.2. In addition, the negative control absorbance should be less than or equal to 0.2. The presence or absence of antibody to FIV is determined by relating the $A_{650}$ value of the sample to the negative control mean. Anything 3 times greater in absorbance intensity than the negative control is regarded as a positive sample.

Deposit

FIV isolate no. 2427 (petaluma strain) has been deposited with the ATCC and assigned number CRL 9761, on Jul. 13, 1988.

Applicants' and their assignees acknowledge their responsibility to replace this culture should it die before the end of the term of a patent issued hereon, 5 years after the last request for a culture, or 30 years, whichever is the longer, and its responsibility to notify the depository of the issuance of such a patent, at which time the deposit will be made irrevocably available to the public. Until that time the deposit will be made available to the Commissioner of Patents under the terms of 37 CFR Section 1–14 and 35 USC Section 112.

Other embodiments are within the following claims.

We claim:

1. A method for detecting an antibody and an antigen in a single biological sample, said method comprising:
   (a) providing an antigen which selectively forms a first immune complex with a sample antibody, said antigen being directly bound to a solid support at a first location;
   (b) providing an antibody which selectively forms a second immune complex with a sample antigen, said antibody being directly bound to said solid support at a second location;
   (c) contacting said first location on said solid support with at least a portion of a biological sample under conditions whereby said first immune complex can form and contacting said second location on said solid support with at least a portion of said sample under conditions whereby said second immune complex can form;
   (d) washing unbound material from said first location and from said second location; and
   (e) separately detecting whether said first immune complex is formed and whether said second immune complex is formed, said first immune complex being detected with a labelled antigen which selectively binds to said first complex and said second immune complex being detected by adding a labelled antibody which selectively binds to said second complex, said labelled antibody being presented to both said first and said second locations.

2. The method of claim 1, wherein said detection of said first immune complex and detection of said second immune complex occur simultaneously.

3. The method of claim 1, wherein said antigen provided in Step (a) is a virus or a viral antigen and said antibody provided in step (b) is capable of selectively forming an immune complex with a virus or a viral antigen.

4. The method of claim 3, wherein each of said viruses is a feline virus.

5. The method of claim 3, wherein each of said viruses is a human virus.

6. The method of claim 5, wherein each of said human viruses is chosen, independently, from the group consisting of a human immunodeficiency virus, a human T-lymphotropic virus, or a hepatitis virus.

7. A method for detecting an antibody to an antigen of a first feline pathogen and an antigen of a second feline pathogen in a single biological sample, said first and second feline pathogens being independently selected from the group consisting of Feline Leukemia Virus (FeLV) and Feline Immune Deficiency Virus (FIV), said method comprising:
   (a) providing an antigen which selectively forms a first immune complex with a sample antibody, said antigen being directly bound to a solid support at a first location;
   (b) providing an antibody which selectively forms a second immune complex with a sample antigen, said antibody being directly bound to said solid support at a second location;
   (c) contacting said first location on said solid support with at least a portion of a biological sample under conditions whereby said first immune complex can form and contacting said second location on said solid support with at least a portion of said sample under conditions whereby said second immune complex can form;
   (d) washing unbound material from said first location and from said second location; and
   (e) separately detecting whether said first immune complex is formed and whether said second immune complex is formed, said first immune complex being detected with a labelled antigen which selectively binds to said first complex and said second immune complex being detected by adding a labelled antibody which selectively binds to said second complex, said labelled antibody being presented to both said first and said second locations.

8. The method of claim 7 in which said first feline pathogen is FIV and said second feline pathogen is FeLV.

9. A kit comprising:
   a) a solid support comprising an antigen which is capable of selectively forming a first immune complex with a sample antibody, said antigen being directly bound to a solid support at a first location; and an antibody, said antibody being capable of selectively forming a second immune complex with a sample antigen, said antibody being directly bound to said solid support at a second location,
   wherein said locations are positioned so that antigen may be contacted with at least a portion of a biological sample whereby said first immune complex can form and said antibody may be contacted with at least a portion of said sample, whereby said second immune complex can form;

b) a complex detector comprising a labelled antigen which selectively binds to said first immune complex, and c) a labelled antibody which selectively binds to said second immune complex when said labelled antibody is presented to both said first and said second locations.

10. The kit of claim 9, wherein said antigen bound at said first location is a virus or a viral antigen and said antibody bound at said second location is capable of selectively forming an immune complex with a virus or a viral antigen.

11. The kit of claim 10, wherein each of said viruses is a feline virus.

12. The kit of claim 10, wherein each of said viruses is a human virus.

13. The kit of claim 12, wherein each of said human viruses is chosen, independently, from the group consisting of a human immunodeficiency virus, a human T-lymphotropic virus, or a hepatitis virus.

14. A kit comprising:

a) a solid support comprising an antigen of a first feline pathogen, wherein said antigen is capable of selectively forming a first immune complex with a sample antibody, said antigen being directly bound to a solid support at a first location; and an antibody to an antigen of a second feline pathogen, wherein said antibody is capable of selectively forming a second immune complex with a sample antigen, said antibody being directly bound to said solid support at a second location, wherein said antigen may be contacted with at least a portion of a biological sample under conditions whereby said first immune complex can form and said antibody may be contacted with at least a portion of said sample, whereby said second immune complex can form;

b) a complex detector comprising a labelled antigen which selectively binds to said first immune complex, and c) a labelled antibody which selectively binds to said second immune complex when said labelled antibody is presented to both said first and said second locations.

15. The kit of claim 14 in which said first feline pathogen is FIV and said second feline pathogen is FeLV.

* * * * *